United States Patent
Woo et al.

(10) Patent No.: US 8,729,279 B2
(45) Date of Patent: May 20, 2014

(54) AGENT FOR PROMOTING OSTEOBLAST DIFFERENTIATION, PHARMACEUTICAL COMPOSITION FOR PROMOTING BONE FORMATION, AND FOOD FOR SPECIAL DIETARY USE CONTAINING AURAPTENE ANALOG AS ACTIVE INGREDIENT

(75) Inventors: Je-Tae Woo, Aichi (JP); Ayaka Hibino, Aichi (JP); Takayuki Yonezawa, Aichi (JP); Midori Asai, Aichi (JP); Toshiaki Teruya, Aichi (JP); Byung-Yoon Cha, Aichi (JP); Kazuo Nagai, Aichi (JP)

(73) Assignee: Erina Co., Inc., Tokyo (JP)

( * ) Notice: Subject to any disclaimer, the term of this patent is extended or adjusted under 35 U.S.C. 154(b) by 0 days.

(21) Appl. No.: 13/581,975

(22) PCT Filed: Feb. 28, 2011

(86) PCT No.: PCT/JP2011/054540
§ 371 (c)(1),
(2), (4) Date: Aug. 30, 2012

(87) PCT Pub. No.: WO2011/108499
PCT Pub. Date: Sep. 9, 2011

(65) Prior Publication Data
US 2013/0102796 A1 Apr. 25, 2013

(30) Foreign Application Priority Data
Mar. 3, 2010 (JP) ................................. 2010-046999

(51) Int. Cl.
C07D 311/00 (2006.01)
C07D 311/02 (2006.01)
(52) U.S. Cl.
USPC .......................................... 549/284; 549/289
(58) Field of Classification Search
USPC ................................................. 549/284, 289
See application file for complete search history.

(56) References Cited

U.S. PATENT DOCUMENTS

| 5,935,996 | A | 8/1999 | Yamaguchi |
| 2008/0119417 | A1 | 5/2008 | Sasaki |
| 2009/0118361 | A1 | 5/2009 | Sasaki |

FOREIGN PATENT DOCUMENTS

| JP | 9-157166 | A | 6/1997 |
| JP | 10-114653 | A | 5/1998 |
| JP | 2006-8625 | A | 1/2006 |
| JP | 2006-83151 | A | 3/2006 |
| JP | 2008-517879 | A | 5/2008 |
| JP | 2009-256350 | A | 11/2009 |
| WO | 2006/042441 | A2 | 4/2006 |
| WO | 2006/077972 | A1 | 7/2006 |
| WO | 2007/132893 | A1 | 11/2007 |

OTHER PUBLICATIONS

Murakami et al. BioFactors 30 (2007) 179-192.*
Kazunori Ogawa, et al., "Evaluation of Auraptene Content in Citrus Fruits and Their Products"; J. Agric. Food Chem., vol. 48, 2000; pp. 1763-1769.
International Search Report w/translation from PCT/JP2011/054540 mailed Apr. 12, 2011 (6 pages).
Wu, Y. et al.; "Antiosteoporotic Activity of Anthraquinones from *Morinda officinalis* on Osteoblasts and Osteoclasts"; Molecules; 2009; vol. 14, No. 1; pp. 573-583 (11 pages).
Kuo, P. et al.; "Osthole-Mediated Cell Differentiation through Bone Morphogenetic Protein-2/p38 and Extracellular Signal-Regulated Kinase 1/2 Pathway in Human Osteoblast Cells"; Journal of Pharmacology and Experimental Therapeutics; 2005; vol. 314, No. 3; pp. 1290-1299 (10 pages).
Kuo, P. et al.; "Bone Morphogenetic Protein-2 and -4 (BMP-2 and -4) Mediates Fraxetin-Induced Maturation and Differentiation in Human Osteoblast-Like Cell Lines"; Biological & Pharmaceutical Bulletin; 2006; vol. 29, No. 1; pp. 119-124 (6 pages).
Prince, M.; "Comparison of Citrus Coumarins on Carcinogen-Detoxifying Enzymes in NRF2 Knockout Mice"; Toxicology Letters; 2009; vol. 185, No. 3; pp. 180-186 (18 pages).
Cesar, T. et al.; "Minor Furanocoumarins and Coumarins in Grapefruit Peel Oil as Inhibitors of Human Cytochrome P450 3A4"; J. Nat. Prod. 2009, 72; pp. 1702-1704 (3 pages).
Tanaka, T. et al.; "Colorectal Cancer Chemoprevention by 2 β-cyclodextrin Inclusion Compounds of Auraptene and 4'-geranyloxyferulic Acid"; Int. J. Cancer; 2010; pp. 830-840 (11 pages).
Krishnan, P. et al.; "Citrus Auraptene Suppresses Cyclin D I and Significantly Delays N-methyl Nitrosourea Induced Mammary Carcinogenesis in Female Sprague-Dawley Rats"; BMC Cancer; Jul. 29, 2009 (12 pages).

(Continued)

*Primary Examiner* — Nizal Chandrakumar
(74) *Attorney, Agent, or Firm* — Osha Liang LLP

(57) ABSTRACT

Agents or pharmaceutical compositions for promoting osteoblast differentiation include purified auraptene or coumarin analogs thereof represented by the following formula 1:

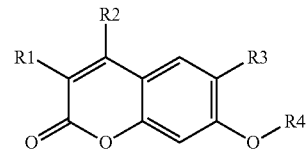

Formula 1 wherein R1 represents a hydrogen, a hydroxy, a methoxy, a methyl, an ethyl, a propyl, a carboxyl, a carboxymethyl, or a carboxyethyl; R2 represents a hydrogen, a hydroxy, a methoxy, a methyl, an ethyl, a propyl, a carboxyl, a carboxymethyl, a carboxyethyl or a coumarinyl; R3 represents a hydrogen, a hydroxy, a methoxy, a methyl, an ethyl, a propyl, a carboxyl, a carboxymethyl or a carboxyethyl; and R4 represents a hydrogen, a $C_1$-$C_{15}$ liner or branched alkyl, an alkenyl, an alkadienyl or an alkatrienyl.

3 Claims, 7 Drawing Sheets

(56) References Cited

OTHER PUBLICATIONS

Soltani, F. et al.; "Auraptene from *Ferula szowitsiana* Protects Human Peripheral Lymphocytes Against Oxidative Stress"; Phytotherapy Research; 2010; pp. 85-89 (5 pages).

Murakami, A.; "Chemoprevention with Phytochemicals Targeting Inducible Nitric Oxide Synthase"; Forum Nutr.; 2009; vol. 61; pp. 193-203 (11 pages).

Lapa, F. et al.; "Antinociceptive Properties of the Hydroalcoholic Extract and the Flavonoid Rutin Obtained from *Polygala paniculata* L. in Mice"; Basic & Clinical Pharmacology & Toxicology; 2009; pp. 306-315 (10 pages).

Tanaka, T. et al.; "Citrus Compounds Inhibit Inflammation- and Obesity-Related Colon Carcinogenesis in Mice"; Nutrition and Cancer; Nov. 10, 2008; pp. 70-80 (12 pages).

Nabekura, T. et al.; "Effects of Chemopreventive Citrus Phytochemicals on Human P-glycoprotein and Multidrug Resistance Protein 1"; European Journal of Pharmacology; 2008; pp. 45-49 (5 pages).

Trzeciakiewicz, A. et al.; "Molecular Mechanism of Hesperetin-7-0-glucuronide, the Main Circulating Metabolite of Hesperidin, Involved in Osteoblast Differentiation"; Journal of Agricultural and Food Chemistry; 2010; pp. 668-675 (8 pages).

Trzeciakiewicz, A. et al.; "Hesperetin Stimulates Differentiation of Primary Rat Osteoblasts Involving the BMP Signalling Pathway"; Journal of Nutritional Biochemistry 21; 2010; pp. 424-431 (8 pages).

Wong, R. et al.; "Effect of Naringin on Bone Cells"; Journal of Orthopaedic Research; Nov. 2006; pp. 2045-2050 (6 pages).

Yamaguchi, M. et al.; "The Bone Anabolic Carotenoid $\beta$-cryptoxanthin Enhances Transforming Growth Factor-$\beta$1-induced SMAD Activation in MC3T3 Preosteoblasts"; Journal of Molecular Medicine 24; 2009; pp. 671-675 (5 pages).

Tang, C., et al.; "Enhancement of Bone Morphogenetic Protein-2 Expression and Bone Formation by Coumarin Derivatives Via p38 and ERK-dependent Pathway in Osteoblasts"; European Journal of Pharmacology 579; 2008; pp. 40-49 (10 pages).

Kudo, Y. et al.; "Evidence for Modulation of Osteocalcin Containing Y-carboxyglutamic Acid Residues Synthesis by Insulin-like Growth Factor-I and Vitamin K2 in Human Osteosarcoma Cell Line MG-63"; European Journal of Endrocrinology; 1998; 138; pp. 443-448 (6 pages).

Avgeri, M. et al.; "Assessment of Bone Mineral Density and Markers of Bone Turnover in Children Under Long-term Oral Anticoagulant Therapy"; J. Pediatr. Hematol. Oncol. 2008; 30; pp. 592-597 (6 pages).

\* cited by examiner

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial
<220> FEATURE:
<223> OTHER INFORMATION: primer
      beta-actin Forward

<400> SEQUENCE: 1
ggctgtattc ccctccatcg                                              20

<210> SEQ ID NO 2
<211> LENGTH: 22
<212> TYPE: DNA
<213> ORGANISM: Artificial
<220> FEATURE:
<223> OTHER INFORMATION: primer
      beta-actin Reverse

<400> SEQUENCE: 2
ccagttggta acaatgccat gt                                           22

<210> SEQ ID NO 3
<211> LENGTH: 18
<212> TYPE: DNA
<213> ORGANISM: Artificial
<220> FEATURE:
<223> OTHER INFORMATION: primer
      ALP Forward

<400> SEQUENCE: 3
actgcgctcc ttagggct                                                18

<210> SEQ ID NO 4
<211> LENGTH: 21
<212> TYPE: DNA
<213> ORGANISM: Artificial
<220> FEATURE:
<223> OTHER INFORMATION: primer
      ALP Reverse

<400> SEQUENCE: 4
```

```
ggcagcgtca gatgttaatt g                                      21

<210> SEQ ID NO 5
<211> LENGTH: 20
<212> TYPE: DNA
<213> ORGANISM: Artificial
<220> FEATURE:
<223> OTHER INFORMATION: primer
      Osteocalcin Forward

<400> SEQUENCE: 5
ggtagtgaac agactccggc                                        20

<210> SEQ ID NO 6
<211> LENGTH: 20
<212> TYPE: DNA
<213> ORGANISM: Artificial
<220> FEATURE:
<223> OTHER INFORMATION: primer
      Osteocalcin Reverse

<400> SEQUENCE: 6
caagcagggt taagctcaca                                        20

<210> SEQ ID NO 7
<211> LENGTH: 20
<212> TYPE: DNA
<213> ORGANISM: Artificial
<220> FEATURE:
<223> OTHER INFORMATION: primer
      Runx2 Forward

<400> SEQUENCE: 7
ccgcacgaca accgcaccat                                        20

<210> SEQ ID NO 8
<211> LENGTH: 20
<212> TYPE: DNA
<213> ORGANISM: Artificial
<220> FEATURE:
<223> OTHER INFORMATION: primer
      Runx2 Reverse

<400> SEQUENCE: 8
cgctccggcc cacaaatctc                                        20

<210> SEQ ID NO 9
<211> LENGTH: 20
<212> TYPE: DNA
<213> ORGANISM: Artificial
<220> FEATURE:
<223> OTHER INFORMATION: primer
      Osterix Forward

<400> SEQUENCE: 9
cccacccttc cctcactcat                                        20

<210> SEQ ID NO 10
<211> LENGTH: 21
<212> TYPE: DNA
<213> ORGANISM: Artificial
<220> FEATURE:
<223> OTHER INFORMATION: primer
      Osterix Reverse

<400> SEQUENCE: 10
ccttgtacca cgagccatag g                                      21
```

```
<210> SEQ ID NO 11
<211> LENGTH: 20
<212> TYPE: DNA
<213> ORGANISM: Artificial
<220> FEATURE:
<223> OTHER INFORMATION: primer
      BMP-2 Forward

<400> SEQUENCE: 11
gctccacaaa cgagaaaagc                                              20

<210> SEQ ID NO 12
<211> LENGTH: 20
<212> TYPE: DNA
<213> ORGANISM: Artificial
<220> FEATURE:
<223> OTHER INFORMATION: primer
      BMP-2 Reverse

<400> SEQUENCE: 12
agcaagggga aaaggacact                                              20

<210> SEQ ID NO 13
<211> LENGTH: 21
<212> TYPE: DNA
<213> ORGANISM: Artificial
<220> FEATURE:
<223> OTHER INFORMATION: primer
      BMP-4 Forward

<400> SEQUENCE: 13
gacttcgagg cgacacttct a                                            21

<210> SEQ ID NO 14
<211> LENGTH: 23
<212> TYPE: DNA
<213> ORGANISM: Artificial
<220> FEATURE:
<223> OTHER INFORMATION: primer
      BMP-4 Reverse

<400> SEQUENCE: 14
gccggtaaag atccctcatg taa                                          23
```

AGENT FOR PROMOTING OSTEOBLAST DIFFERENTIATION, PHARMACEUTICAL COMPOSITION FOR PROMOTING BONE FORMATION, AND FOOD FOR SPECIAL DIETARY USE CONTAINING AURAPTENE ANALOG AS ACTIVE INGREDIENT

CROSS REFERENCE TO RELATED APPLICATIONS

This is a national stage application based on PCT/JP2011/054540, filed on Feb. 28, 2011, which claims priority to Japanese Patent Application No. JP2010-046999, filed on Mar. 3, 2010. This application claims the priority of these prior applications and incorporates their disclosures by reference in their entireties.

TECHNICAL FIELD

The present invention relates to an agent for promoting osteoblast differentiation containing, as an active ingredient, auraptene or an analog thereof contained in citrus fruits, a pharmaceutical composition for promoting bone formation, food additive, health food (food for special dietary use) and the like containing the same.

BACKGROUND ART

Some of ingredients contained in various citrus fruits are known to have a variety of bioactivities. Auraptene, a kind of coumarin compounds, is known to have bioactivity such as antitumor activity, antioxidative activity, anti-inflammatory action, PPAR agonist activity, antibacterial activity, antiplatelet activity and antileishmanial activity and there have been proposed an ameliorating agent for metabolic syndrome using the effect of auraptene (Patent Literatures 1: Domestic Re-publication of PCT International Application No. 07-132893 and 2: Domestic Re-publication of PCT International Application No. 06-077972), a drug for preventing or treating neurotransmission disorder (Patent Literature 3: Japanese PCT National Publication No. 2008-517879), an inhibitor of Epstein-Barr virus early antigen induction (Patent Literature 4: Japanese Patent Application Laid-Open (JP-A) No. 09-157166) and the like.

In addition, as an ingredient of citrus fruits having an effect of promoting osteoblast differentiation, hesperetin (Non-Patent Literatures 1 and 2), naringin (Non-Patent Literature 3) and β-cryptoxanthin (Non-Patent Literature 4) are reported. Coumarin compounds are described in Non-Patent Literatures 5 to 9.

JP-A No. 2006-083151 (Patent Literature 5) describes a composition for preventing and improving osteoporosis characterized by containing an extract of *Citrus unshiu* fruit and pericarp, which is based on the bone resorption inhibition effect due to inhibition of osteoclast differentiation by β-cryptoxanthin and hesperidin.

JP-A No. 2006-008625 (Patent Literature 6) describes a bone metabolism improving agent including summer orange (Hyuga natsu; *C. tamurana*) treatment product. As the effects on osteoblasts, the growth stimulating effect and IL-6 production promoting effect are described. However, the differentiation promoting effect is not described.

Thus, literatures reporting the osteoblast differentiation promoting effect or bone formation promoting effect of auraptene and an analog thereof cannot be found.

CITATION LIST

Patent Literature

Patent Literature 1: Domestic Re-publication of PCT International Application No. 07-132893

Patent Literature 2: Domestic Re-publication of PCT International Application No. 06-077972

Patent Literature 3: Japanese PCT National Publication No. 2008-517879

Patent Literature 4: Japanese Patent Application Laid-Open (JP-A) No. 09-157166

Patent Literature 5: JP-A No. 2006-083151

Patent Literature 6: JP-A No. 2006-008625

Non-Patent Literature

Non-Patent Literature 1: Cesar T B et al., J Nat. Prod. 2009 September; 72(9):1702-4.

Non-Patent Literature 2: Tanaka T et al., Int J Cancer. 2010 Feb. 15; 126(4):830-40

Non-Patent Literature 3: Krishnan P et al., BMC Cancer. 2009 Jul. 29; 9:259

Non-Patent Literature 4: Soltani F et al., Phytother Res. 2010 January; 24(1):85-9

Non-Patent Literature 5: Murakami A, Forum Nutr. 2009; 61:193-203. Epub 2009 Apr. 7

Non-Patent Literature 6: Lapa Fda R, et al., Basic Clin Pharmacol Toxicol. 2009 Apr; 104(4):306-15. Epub 2009 March 5

Non-Patent Literature 7: Prince M, et al., Toxicol Lett. 2009 Mar. 28; 185(3):180-6. Epub 2008 Dec. 30

Non-Patent Literature 8: Tanaka T, et al., Nutr Cancer. 2008; 60 Suppl 1:70-80

Non-Patent Literature 9: Nabekura T, et al., Eur J. Pharmacol. 2008 Dec. 14; 600(1-3):45-9. Epub 2008 Oct. 21

SUMMARY OF INVENTION

Problem to be Solved by the Invention

An object of the present invention is to provide a novel use of auraptene and coumarin analogues thereof and to provide an agent for promoting osteoblast differentiation, pharmaceutical composition for promoting bone formation, food for special dietary use and the like with high safety and efficacy.

Solution to Problem

The present inventors found that auraptene and coumarin analogues thereof contained in citrus fruits have an effect of promoting osteoblast differentiation, thereby completing the present invention.

Accordingly, the present invention provides an agent for promoting osteoblast differentiation containing a purified coumarin compound represented by the following formula 1:

[Chemical Formula 1]

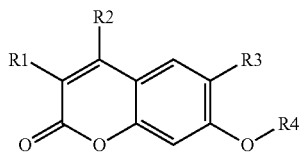

Formula 1 wherein R1 represents a hydrogen atom, a hydroxy group, a methoxy group, a methyl group, an ethyl group, a propyl group, a carboxyl group, a carboxymethyl group or a carboxyethyl group;

R2 represents a hydrogen atom, a hydroxy group, a methoxy group, a methyl group, an ethyl group, a propyl group, a carboxyl group, a carboxymethyl group, a carboxyethyl group or a coumarinyl group;

R3 represents a hydrogen atom, a hydroxy group, a methoxy group, a methyl group, an ethyl group, a propyl group, a carboxyl group, a carboxymethyl group or a carboxyethyl group; and R4 represents a hydrogen atom, a $C_1$-$C_{15}$ liner or branched alkyl group, an alkenyl group, an alkadienyl group or an alkatrienyl group.

R4 is preferably an isobutenyl group, a prenyl group or a geranyl group.

Examples of the compound of the formula 1 include, for example:

1. auraptene (2H-1-benzopyran-2-one, 7-[[(2E)-3, 7-dimethyl-2,6-octadiene-1-yl]oxy]-; another name: 7-(geranyloxy)coumarin) represented by the following formula 2:

[Chemical Formula 2]

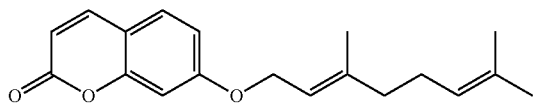

Formula 2

2. A compound represented by the following formula 3, P02C10 (2H-1-benzopyran-2-one, 7-[(3,7-dimethyl-2, 6-octadienyl)oxy]-4-methyl-, (E)-; another name: 4-methyl-7-(geranyloxy)coumarin):

[Chemical Formula 3]

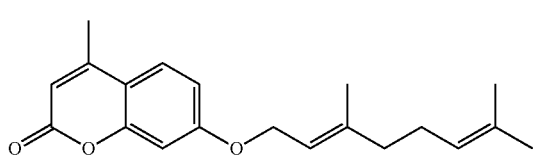

Formula 3

3. A compound represented by the following formula 4, P02D10 (2H-1-benzopyran-2-one, 7-[(3,7-octadiene-1-yl) oxy]-4-phenyl-):

[Chemical Formula 4]

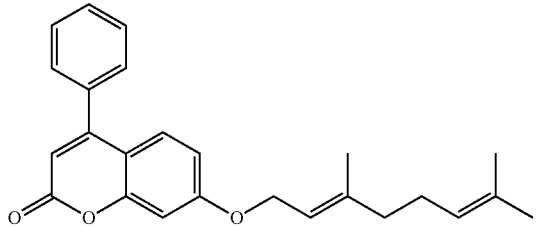

Formula 4

4. A compound represented by the following formula 5, P02H08 (2H-1-benzopyran-2-one, 7-[(3-methyl-2-butene-1-yl) oxy]-; another name: 7-(isopentenyloxy)coumarin):

[Chemical Formula 5]

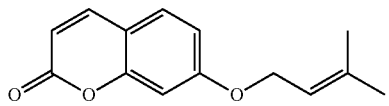

Formula 5

5. A compound represented by the following formula 6, P03G10 (2H-1-benzopyran-2-one, 4-methyl-7-[(2-methyl-2-propene-1-yl)oxy-):

[Chemical Formula 6]

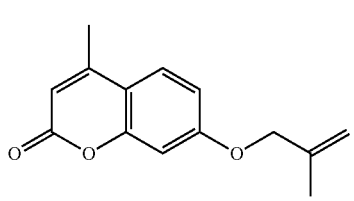

Formula 6

6. A compound represented by the following formula 7, P06C11 (2H-1-benzopyran-2-one, 6-hydroxy-7-[(3-methyl-2-butene-1-yl)oxy]-; another name: prenyletin or 7-O-prenylesculetin):

[Chemical Formula 7]

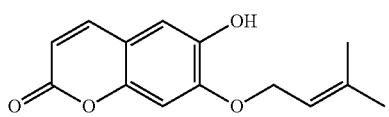

Formula 7

7. A compound represented by the following formula 8, P18E03 (2H-1-benzopyrene-3-acetate, 4-methyl-7-[(2-methyl-2-propene-1-yl)oxy]-2-oxo-, methyl ester):

[Chemical Formula 8]

Formula 8

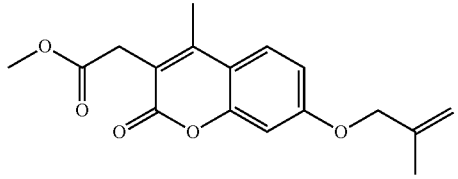

8. A compound represented by the following formula 9, P16D11([3,4'-bi-2H-1-benzopyran]-2,2'-dion, 7'-hydroxy-):

[Chemical Formula 9]

Formula 9

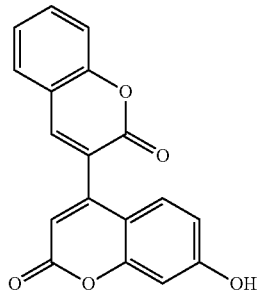

In addition, the present invention also provides a pharmaceutical composition for promoting bone formation containing, as an active ingredient, the agent for promoting osteoblast differentiation as stated above, a food for special dietary use and food additive containing the agent for promoting osteoblast differentiation as stated above and a food or drink added with the food additive.

Advantageous Effects of Invention

Each of the compounds used in the present invention is contained in citrus fruits and the like in a large amount and has long been eaten, which ensures a very high level of safety of the compounds. Besides, the compounds are all easily available. Although, as a naturally-occurring compound, there have been many reports showing that genistein, an isoflavone compound, has an osteoblast differentiation promoting action (JP-A No. 10-114653, etc.), each of the above compounds used in the present invention has stronger activity than genistein.

In addition, each of the above compounds has a potent osteoblast differentiation promoting action comparable to an osteogenic factor (Bone morphogenetic protein 2; BMP-2) which is a cytokine known for the potent bone formation promoting action. Due to the potent action of inducing bone formation, BMP is expected to be applied to many osteopenic diseases. However, since BMP is a protein, there are problems such as (1) quite high production costs and (2) stability problems and difficulty in quality control. In contrast, since auraptene and coumarin analogues thereof used in the present invention are naturally-occurring low molecular weight compounds and are highly stable, they are easy in handling and quality control. Besides, they can be produced at low cost. Therefore, an agent for promoting osteoblast differentiation, pharmaceutical composition for promoting bone formation and the like of the present invention, which can provide an action similar to BMP, are quite useful for preventing and treating osteopenic diseases.

The agent for promoting osteoblast differentiation and pharmaceutical composition for promoting bone formation of the present invention promote cell differentiation without exerting any influence on cell proliferation and survival, and can be used as a pharmaceutical composition for preventing or treating many osteopenic diseases (e.g., osteoporosis, rheumatoid arthritis, periodontal disease, Paget's disease, bone metastasis of cancer and so on) of humans and animals other than humans. In addition, the agent for promoting osteoblast differentiation and pharmaceutical composition for promoting bone formation of the present invention can also be used for promoting bone formation and bone regeneration at bone defective parts, promoting alveoloplasty and alveolar bone regeneration as a pretreatment for the implant tooth implantation and the like. Further, the agent for promoting osteoblast differentiation and pharmaceutical composition for promoting bone formation of the present invention can also be used for devices introduced surgically when bones, teeth, joints and the like are damaged, or they may be used by including in an implant or by coating an implant.

Further, the agent for promoting osteoblast differentiation of the present invention can also be used as a food additive and can be applied to a food for special dietary use, food or drink, sanitary goods (including quasi-drug products such as toothpaste) and the like having a bone-enhancing effect.

BRIEF DESCRIPTION OF DRAWINGS

FIG. 2-1 is a figure (panels A to F) showing the effects of each of the compounds on osteoblast initial differentiation. Examined compounds are auraptene (formula 2) in panel A; P02C10 (formula 3) in panel B; P02C10 (formula 4) in panel C; P02D10 (formula 5) in panel D; P02H08 (formula 6) in panel E; PP06C11 (formula 7) in panel F; P18E03 (formula 8) in panel G; and P16D11 (formula 9) in panel H. In each panel, an open bar and a solid bar represent cell viability and ALP activity, respectively. Compared with control, ** represents a significant difference of p<0.005 and * represents a significant difference of p<0.05.

FIG. 2-2 is a figure (panels G and H) showing the effects of each of the compounds on osteoblast initial differentiation. Explanation of the bars is the same as in FIG. 2-1.

FIG. 7-1 is a figure (panels A to F) showing the action of each of the compounds on osteoclast differentiation. Examined compounds are auraptene (formula 2) in panel A; P02C10 (formula 3) in panel B; P02C10 (formula 4) in panel C; P02D10 (formula 5) in panel D; P02H08 (formula 6) in panel E; PP06C11 (formula 7) in panel F; and P18E03 (formula 8) in panel G. In each panel, an open bar and a solid bar represent cell viability and TRAP activity, respectively. Compared with control, ** represents a significant difference of p<0.005 and * represents a significant difference of p<0.05.

FIG. 7-2 is a figure (panel G) showing the action of each of compounds on osteoclast differentiation. Explanation of the graph is the same as in FIG. 7-1.

DESCRIPTION OF EMBODIMENTS

Figure 1:
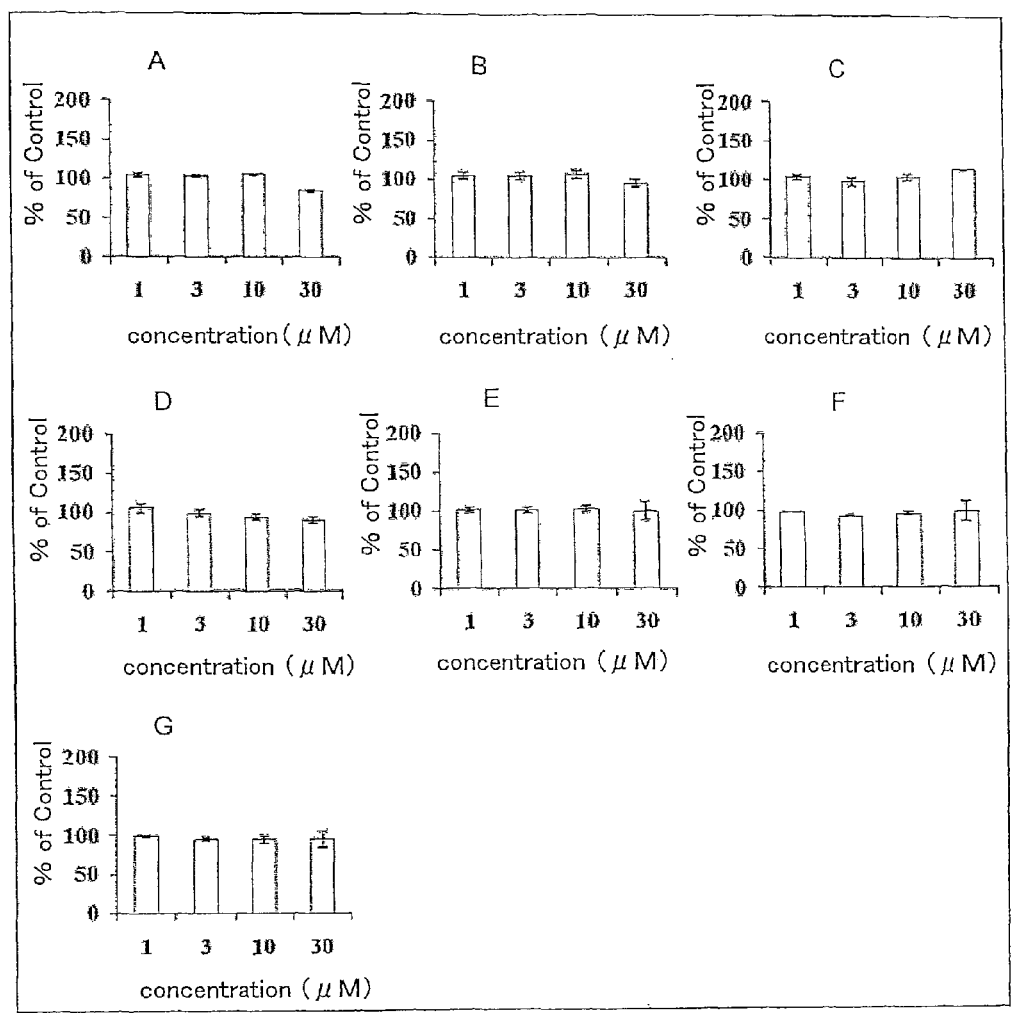
FIG. 1 is a figure showing the effects of each of the compounds on osteoblast proliferation. Examined compounds are auraptene (formula 2) in panel A; P02C10 (formula 3) in panel B; P02C10 (formula 4) in panel C; P02D10 (formula 5) in panel D; P02H08 (formula 6) in panel E; PP06C11 (formula 7) in panel F; and P18E03 (formula 8) in panel G.

The agent for promoting osteoblast differentiation of the present invention contains, as an active ingredient, at least one of the compounds of the formula 1:

[Chemical Formula 10]

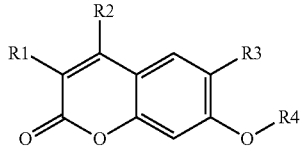

Formula 1 wherein R1 to R4 are as defined above.

These compounds are known to be contained in a wide range of citrus fruits. In particular, there have been many reports regarding auraptene. For example, J. Agric. Food Chem. 2000 May; 48(5):1763-9, states the aurapten contents of 77 kinds of citrus fruits. Auraptene is contained in peels (up to about 1.5 mg/g dry weight) and in fruits (up to about 0.5 mg/kg dry weight) of citrus, and C. hassaku, C. medioglobosa, C. natsudaidai, C. ampullacea, C. pseudo-aurantium, C. wilsonii and the like contain auraptene in a large amount. In addition, auraptene is known to be also contained in processed food of citrus such as commercially available grapefruit juice (0.11 to 0.14 mg/100 g) and marmalade (0.35 to 0.38 mg/100 g).

Therefore, coumarin compounds used in the present invention may be isolated or purified from such citrus or processed food of citrus by known methods, and may also be prepared by a synthetic method. Purified products of the compounds represented by the formula 2 to formula 9 are all commercially available, so these purified products may also be used.

Among these compounds, the compound represented by the formula 2 (auraptene), formula 3, formula 5, formula 6 or formula 9 is preferred and the compound represented by the formula 2, formula 3 or formula 9 is most preferred.

While the agent for promoting osteoblast differentiation of the present invention contains at least one of the above compounds as an active ingredient, a mixture of two or more may be used in some cases. The agent for promoting osteoblast differentiation can be used for preparing a pharmaceutical composition and the like. In addition, for example, the agent for promoting osteoblast differentiation can be used for a screening assay to determine whether a tested compound has a differentiation inhibitory activity, in which addition of the agent for promoting osteoblast differentiation to a culture medium promotes differentiation of cultured osteoblasts. The agent for promoting osteoblast differentiation can also be used for an assay to determine whether cells have a capacity to differentiate into osteoblasts by culturing the cells with the added agent for promoting osteoblast differentiation, and so on. Additionally, the agent for promoting osteoblast differentiation can be used as an adjunct for inducing osteoblasts effectively in order to analyze various functions of osteoblasts or in order to induce bone regeneration in vitro.

The pharmaceutical composition for promoting bone formation of the present invention contains the agent for promoting osteoblast differentiation of the present invention as an essential component, and as a physiologically or pharmaceutically acceptable additive, the pharmaceutical composition for promoting bone formation may additionally contains various components (e.g., excipients, disintegrators, lubricants) known in the field of pharmaceutical technology. Examples of the excipients include, lactose, sucrose, glucose, sorbitol, lactitol; cornstarch, potato starch, crystalline cellulose; light silica gel, aluminum silicate, magnesium aluminometasilicate, and calcium hydrogen phosphate. Further, examples of the disintegrators include starches mentioned above, carboxymethyl cellulose (CMC), hydroxypropyl cellulose (HPC) and polyvinyl pyrrolidone. Additionally, examples of the lubricants include sucrose fatty acid ester, calcium stearate and magnesium stearate.

Further, the pharmaceutical composition of the present invention can contain other known pharmaceutical active ingredient(s) as well. For example, an ingredient know to be effective for osteopenic diseases (agent for promoting bone formation, bone resorption inhibitor and the like) can be further included. Examples of these ingredients include, calcium preparations, vitamin D preparations, vitamin K preparations, parathyroid hormones, estrogen preparations, bisphosphonates, ipriflavones, fluorine compounds, prostaglandins, transforming growth factor (TGF-β), insulin-like growth factors-1 and -2 (IGF-1 and IGF-2), fibroblast growth factor (FGF) and bone morphogenetic protein (BMP).

The pharmaceutical composition of the present invention can be formulated according to known methods in the field of pharmaceutical technology to prepare a pharmaceutical composition in a desired formulation such as tablets, granules, capsules, powders, external preparations, sprays, film preparations and injections. Also intended are, for example, formulations shaped into an appropriate form by mixing with an appropriate carrier (artificial bone) such as bone matrix of collagen, calcium phosphate and polyethylene glycol copolymers, ones mixed with or coated on a dental implant and the like.

The pharmaceutical composition of the present invention can be administered to humans and various animals other than humans such as mammals, birds and fishes. Examples of the applications include prevention and treatment of various osteopenic diseases (e.g., osteoporosis, rheumatoid arthritis, periodontal disease, Paget's disease, bone metastasis of cancer), promotion of bone formation and bone regeneration at damaged or defective parts of bones, teeth, joints and the like, and promotion of alveoloplasty and alveolar bone regeneration as a pretreatment for the dental implant implantation.

The pharmaceutical composition of the present invention may be administered by any known route. For example, any route such as oral, percutaneous, injection, enteral or rectal administration can be selected. Such a route as implantation with bone matrix by surgery is also possible. The oral administration is preferred.

The effective dose of the pharmaceutical composition of the present invention differs depending on the type, age, body weight, physical condition and the like of the subject, and a dose suitable for each subject can be administered depending on them. In cases of administrating to a mammal, the dose can be 0.0001 to 1,000 mg/kg/day and preferably 0.001 to 100 mg/kg/day, for example. Incases of administrating to a human, in general, the daily amount of active ingredient is 0.001 mg to 5,000 mg, and desirably 0.01 mg to 500 mg. Such a daily dose can be administered once or divided into several doses.

In addition, the pharmaceutical composition of the present invention may be used in combination with other pharmaceuticals.

Moreover, the agent for promoting osteoblast differentiation of the present invention can be used as a food additive. The food additive may contain other known ingredients suitable for food in addition to the agent for promoting osteoblast differentiation of the present invention. Such a food additive may be added to beverages or foods (food or drink) in order to improve functions of the food or drink. Production methods of such a food additive and food or drink are known to those skilled in the art. In addition, the agent for promoting osteoblast differentiation of the present invention may be used by being included as a component in quasi-drug products such as toothpaste and sanitary goods.

EXAMPLES

In Examples, the following reagents and the like were used.

Auraptene was purchased from Wako Pure Chemical Industries, Ltd. (Lkt Labs. Inc.). Other test compounds were all purchased from Summit Pharmaceuticals International Corporation. MC3T3-E1 cells (a pre-osteoblastic cell line derived from embryonic mouse calvaria; cell No. RCB1126) were purchased from RIKEN Cell Bank. α-Minimum essential medium (α-MEM) was purchased from INVITROGEN Corporation (Catalog No. 11900-024). Other reagents were purchased from Wako Pure Chemical Industries, Ltd. or SIGMA Chemical company. 96-well microplates were purchased from Nunc corporation (Catalog No. 161093).

1. Effect of Auraptene on Osteoblast Proliferation

The effect on osteoblast proliferation was determined by the following method.

MC3T3-E1 cells were suspended in α-MEM and plated on each well of a 96-well microplate at a concentration of $2 \times 10^3$ cells/well. After overnight incubation in 10% fetal bovine serum (FBS)-containing α-MEM under a condition of 37° C. and 5% $CO_2$, the culture medium was replaced with 10% FBS-containing α-MEM containing a compound at a concentration of 1, 3, 10 or 30 µM and cultured for 3 days. The cells cultured in the same manner using the medium containing the same amount of solvent only were used as a control.

Added was 3-(4,5-Dimethylthiazol-2-yl)-2,5-diphenyltetrazolium bromide (MTT) (5 mg/ml in PBS) in one-tenth amount of the culture medium 2 hours before the completion of incubation. After 2-hour cultivation, the medium was removed, formazan formed by viable cells was dissolved in DMSO and the absorbance at 570 nm (reference wavelength of 630 nm) was measured with a plate reader. The relative cell numbers were determined by calculating the values taking the control as 100 (average plus or minus standard deviation of 4 wells or more; the same hereinafter).

The results are shown in FIG. 1. Treatment with auraptene, or any other coumarin compound tested, caused little change in cell number of MC3T3-E1 cells which are mouse pre-osteoblastic cells. This indicates that auraptene and coumarin analogues thereof do not significantly affect osteoblast proliferation.

2. Effects on Initial Osteoblast Differentiation

MC3T3-E1 cells which are mouse pre-osteoblastic cells were suspended in α-MEM and plated on each well of a 96-well microplate at a concentration of $5 \times 10^3$ cells/well. After 2-day pre-incubation in 10% FBS-containing α-MEM under a condition of 37° C. and 5% $CO_2$, the culture medium was replaced with 10% FBS-containing α-MEM containing a compound at a concentration of 1, 3, 10, 30 or 100 µM and the cells were cultured for 6 days. During the incubation, the culture medium was replaced once in every 3 days. The cells cultured in the same manner using the medium without coumarin compounds were used as a control.

At the end of incubation, the cell number was measured by the same method as above using a MTT reagent and the value was calculated by taking the control as 100.

In addition, the activity of alkaline phosphatase (ALP), a marker enzyme of initial osteoblast differentiation, was measured by the following method. After incubation, the cells were fixed with cold methanol, and the dishes were dried. 100 µl of buffer of pH 8.5 containing 2 mM magnesium chloride and 100 mM Tris-HCl, with 6.7 mM p-nitrophenylphosphate as a substrate, was dispensed in each well and allowed to react at 37° C. for 30 minutes. Then, 100 μl of 0.1 N sodium hydroxide was added to terminate the reaction, followed by measurement with a plate reader of the absorbance at 405 nm, which was determined to be the ALP activity. The value was calculated by taking the control as 100.

Figures 1, 2:
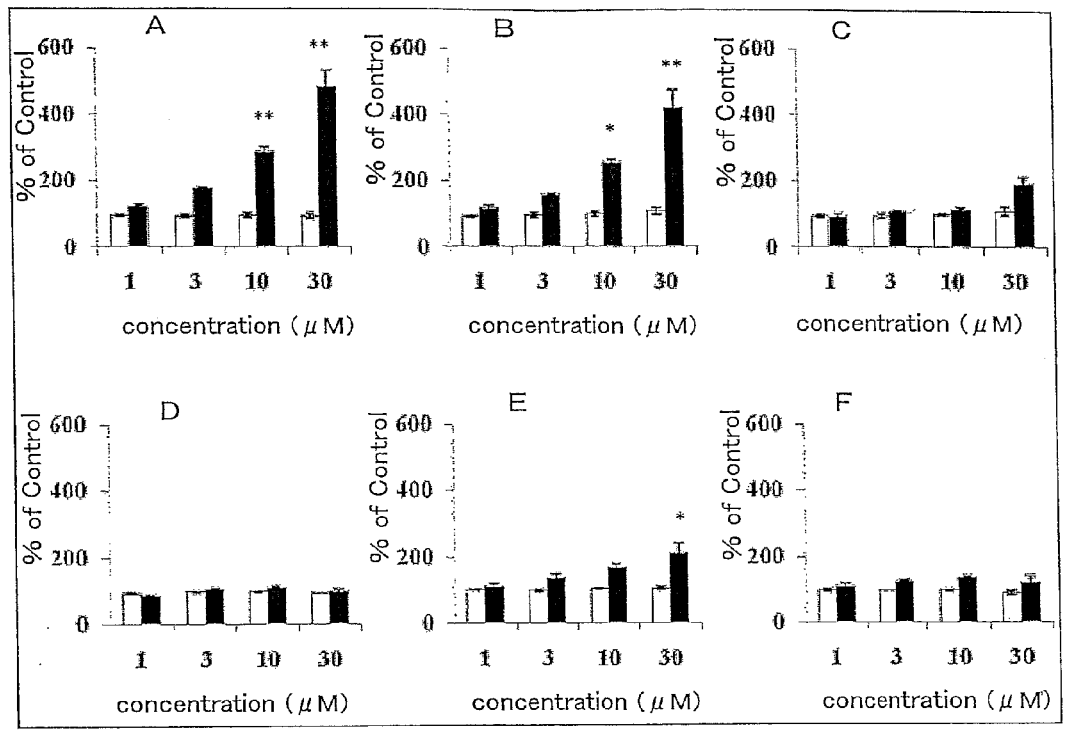
Figure 2:
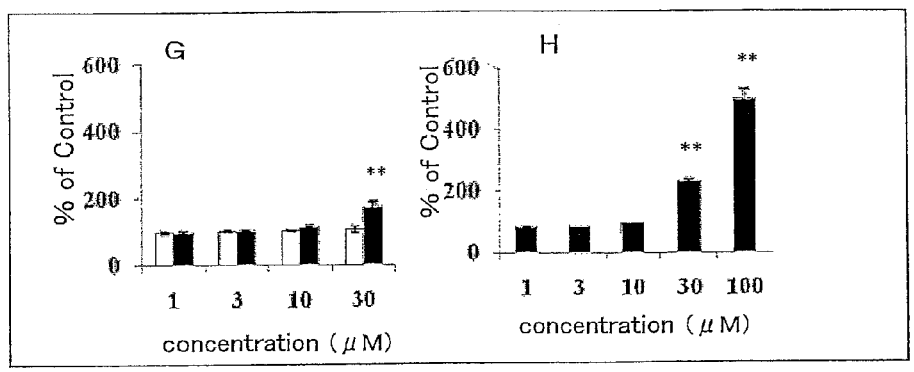

The results are shown in FIG. 2-1 and FIG. 2-2. Although treatment with any coumarin compound such as auraptene caused little influence on cell viability of MC3T3-E1 cells (FIG. 2, the open bar in each panel), the ALP activities were increased in a concentration-dependent manner (FIG. 2, the solid bar in each panel). This indicates that coumarin compounds such as auraptene promote initial osteoblast differentiation without affecting the cell number.

3. Effects on Osteoblast Calcification MC3T3-E1 cells were suspended in α-MEM and plated in each well of a 96-well microplate at a concentration of $5 \times 10^3$ cells/well and pre-incubated for 2 days in 10% FBS-containing α-MEM under a condition of 37° C. and 5% $CO_2$. Thereafter, the culture medium was replaced with 10% FBS-containing α-MEM containing a compound at a concentration of 1, 3, 10 or 30 μM, 50 μg/ml ascorbic acid and 10 mM β-glycerophosphoric acid, and the cells were cultured for 10 days. During the incubation, the culture medium was changed once in every 3 or 4 days.

After incubation, the cells were fixed with 70% ethanol, the dishes were dried, and calcium deposits were stained with a 1% alizarin red S solution. The image of the stained plate was obtained using a scanner. In addition, the degree of stain (degree of calcification) was evaluated by naked eyes.

Figure 3:
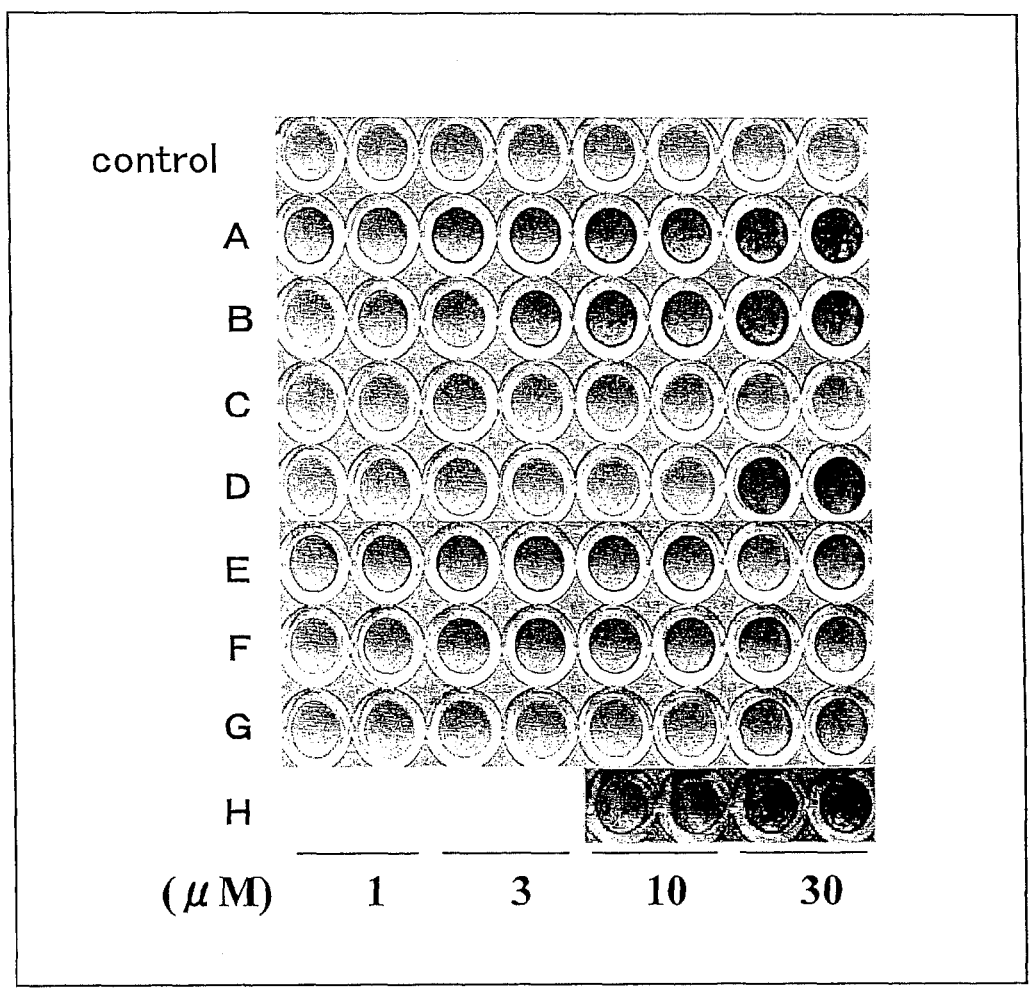
FIG. 3 is a figure showing the effects of each of the compounds on osteoblast calcification. Examined compounds are auraptene (formula 2) in line A; P02C10 (formula 3) in line B; P02C10 (formula 4) in line C; P02D10 (formula 5) in line D; P02H08 (formula 6) in line E; PP06C11 (formula 7) in line F; P18E03 (formula 8) in line G; and P16D11 (formula 9) in line H.

The results are shown in FIG. 3 and Table 1.

TABLE 1

| concentration (μM) | 1 | | 3 | | 10 | | 30 | |
|---|---|---|---|---|---|---|---|---|
| control | − | − | − | − | − | − | − | − |
| auraptene | ± | ± | + | + | ++ | ++ | +++ | +++ |
| compound P02C10 | − | − | − | + | ± | ++ | +++ | +++ |
| compound P02D10 | − | − | − | − | − | − | − | − |
| compound P02H08 | − | − | − | − | − | − | +++ | +++ |
| compound P03G10 | ± | ± | ± | ± | + | + | ± | ++ |
| compound P06C11 | − | − | ± | ± | + | + | + | + |
| compound P18E03 | − | − | − | − | − | ± | + | + |
| compound P16D11 | / | / | / | / | ± | ++ | +++ | +++ |

/: not tested

Osteoblasts produce bone matrix proteins along with the progression of differentiation and further deposit calcium to cause calcification. The calcified portions are stained red by alizarin red staining which stains calcium. When MC3T3-E1 cells which are mouse pre-osteoblastic cells were treated with coumarin compounds such as auraptene, the calcified portions stained red were remarkably increased compared with control. This indicates that coumarin compounds such as auraptene promote calcification by osteoblasts and promote later differentiation of osteoblasts as well.

4. Comparison with Action of BMP-2 and Effect of BMP Signal Inhibitor

Basically in the same manner as above ("2. Effects on Initial Osteoblast Differentiation"), comparison with the action of a bone morphogenetic protein (BMP-2) which is a known agent for promoting osteoblast differentiation, and examination of the inhibitory effects by Noggin and Dorsomorphin, both of which are BMP inhibitors, were performed.

BMP-2 and auraptene were added at 25 ng/ml and 30 μM, respectively. Upon the addition of the sample, the cells were cultured for 6 days in the presence or absence of 10 ng/ml Noggin, a BMP inhibitor, or 1 μM Dorsomorphin, an inhibitor of type I BMP receptor (ALK) (the above concentrations are the final concentrations), and the ALP activities were measured in the same manner as above. BMP-2, Noggin and Dorsomorphin were all purchased from Wako Pure Chemical Industries, Ltd.

Figure 4:
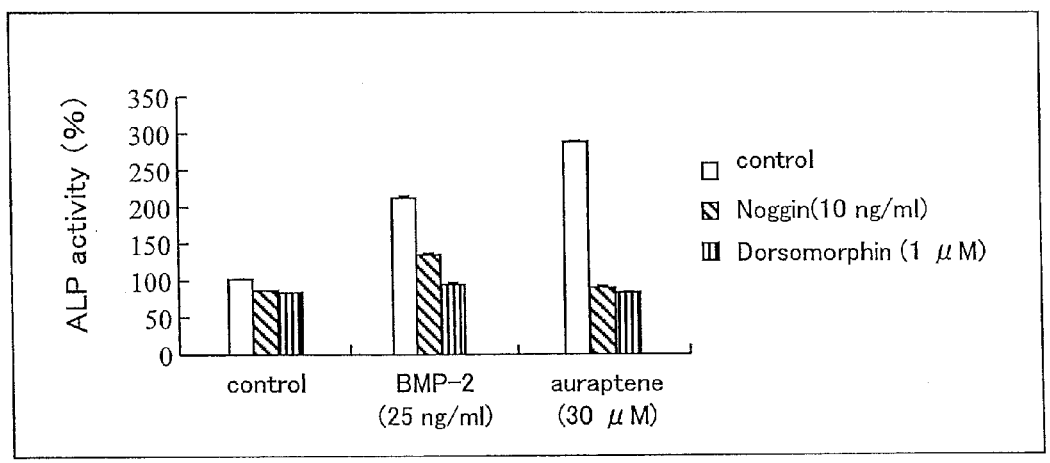
FIG. 4 is a figure showing comparison of osteoblast differentiation promoting action of auraptene with that of BMP-2. For each of control, BMP-2 and auraptene, an open bar represents the result of control (without an inhibitor), a hatched bar represents the results of the addition of Noggin, and a striped bar represents the results of the addition of Dorsomorphin.

The results are shown in FIG. 4.

BMP is a cytokine known as a strong bone morphogenetic factor. It was demonstrated that the effect of promoting ALP activity equivalent to or more than that with BMP-2 (25 ng/ml) was recognized with the auraptene (30 μM) treatment (FIG. 4). This indicates that auraptene has a strong osteoblast differentiation promoting action comparable to BMP-2.

In addition, the effect of promoting ALP activity by auraptene was, as the effect of promoting the ALP activity by BMP-2, diminished by Noggin (10 ng/ml), a BMP inhibitor, and Dorsomorphin (1 μM), an inhibitor of type I BMP receptor (ALK). This indicates that BMP is involved in the effect of promoting ALP activity (osteoblast differentiation promoting action) by auraptene.

According to the results mentioned above, coumarin compounds such as auraptene promote osteoblast differentiation from initial to later stages without affecting osteoblast proliferation and further enhance calcification. Thus, it is believed that coumarin compounds such as auraptene have an bone formation-promoting action.

Accordingly, the agent for promoting osteoblast differentiation, the pharmaceutical composition for promoting bone formation and the like of the present invention, which are naturally-occurring low molecular weight compounds and highly safe and stable, and which can exert an equivalent effect as BMP, are expected to provide the effects beneficial for preventing and treating many osteopenic diseases such as osteoporosis, rheumatoid arthritis, periodontal disease, Paget's disease and bone metastasis of cancer, and are quite useful.

5. Effects on Expression of Various Genes Related to Osteoblast Differentiation

The effects on the expression of various genes related to osteoblast differentiation were analyzed using the real-time RT-PCR method.

MC3T3-E1 cells were plated in each well of a 6-well plate (Greiner) at a concentration of $1.5 \times 10^5$ cells/well and cultured in the same manner as above. After reaching confluent, the culture medium was replaced with the culture medium containing auraptene (30 μM) or BMP-2 (50 ng/ml) and cultured for 0 to 14 days. After incubation, the culture medium was removed and the cells were washed with PBS. Thereafter, "ISOGEN" (trade name, Wako Pure Chemical Industries, Ltd.) was added in an amount of 1 ml/well and the cells were collected. RNA purification was conducted according to the protocol described in the package insert of "ISOGEN".

Reverse transcription was performed using "PrimeScript RT-PCR Kit" (trade name, TaKaRa) with 2 μg of purified RNA according to the protocol described in the package insert, thereby synthesizing the cDNA sample.

Real-time PCR was performed using "FastStart Universal SYBR Green Master (Rox)" (trade name, Roche) according to the protocol described in the package insert under the following conditions: incubation at 50° C. for 2 min and at 95° C. for 10 min, followed by 50 cycles of 15 sec at 95° C.

and 1 min at 60° C. Data were analyzed with "ABI PRISM 7300 sequence detection system" (trade name, Applied Biosystems).

Primers used were as described in the following Table 2.

TABLE 2

| gene | forward (5'-3') | reverse (5'-3') |
|---|---|---|
| β-actin | GGCTGTATTCCCC TCCATCG Seq. ID No. 1 | CCAGTTGGTAACA ATGCCATGT Seq. ID No. 2 |
| ALP | ACTGCGCTCCTTA GGGCT Seq. ID No. 3 | GGCAGCGTCAGAT GTTAATTG Seq. ID No. 4 |
| osteocalcin | GGTAGTGAACAGA CTCCGGC Seq. ID No. 5 | CAAGCAGGGTTAA GCTCACA Seq. ID No. 6 |
| Runx2 | CCGCACGACAACC GCACCAT Seq. ID No. 7 | CGCTCCGGCCCAC AAATCTC Seq. ID No. 8 |
| Osterix | CCCACCCTTCCCT CACTCAT Seq. ID No. 9 | CCTTGTACCACGAG CCATAGG Seq. ID No. 10 |
| BMP-2 | GCTCCACAAACGAG AAAAGC Seq. ID No. 11 | AGCAAGGGGAAAAG GACACT Seq. ID No. 12 |
| BMP-4 | GACTTCGAGGCGAC ACTTCTA Seq. ID No. 13 | GCCGGTAAAGATCC CTCATGTAA Seq. ID No. 14 |

Data analysis was performed as follows using β-actin as an endogenous control gene by the comparative Ct method.

$\Delta$ Ct=(Ct of target gene)−(Ct of endogenous control gene)

$\Delta\Delta$ Ct=($\Delta$ Ct of target sample)−($\Delta$ Ct of reference sample)

Relative expression level of target gene of target sample to that of reference sample=$2^{(-\Delta\Delta^{Ct})}$ The results are shown in FIG. 5A to FIG. 5F.

(1) Expression of Marker Genes of Osteoblast Differentiation

Figure 5A:
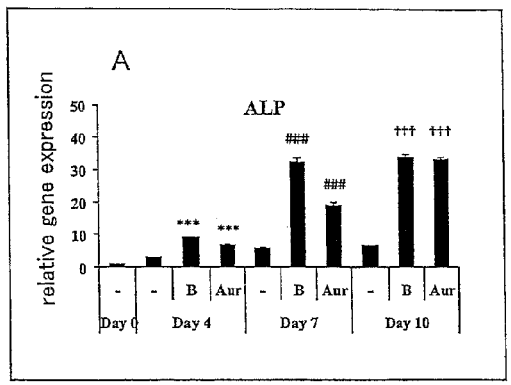
FIG. 5A is a figure showing the action of auraptene on the expression of an bone formation-related gene (ALP). In each panel of FIGS. 5A to 5F, "-" represents control, "B" represents BMP-2 (50 ng/ml) treatment, and "Aur" represents auraptene (30 µM) treatment. Compared with control after 4 days,  represents a significant difference of p<0.005 and * represents a significant difference of p<0.001; compared with control after 7 days, # represents a significant difference of p<0.05 and ### represents a significant difference of p<0.001; and compared with control after 10 days, + represents a significant difference of p<0.05 and +++ represents a significant difference of p<0.001.
Figure 5B:
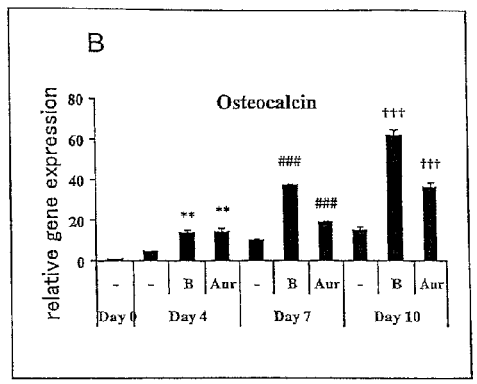
FIG. 5B is a figure showing the action of auraptene on the expression of an bone formation-related gene (Osteocalcin). Explanation of the graph is the same as in FIG. 5A.

As is the case with the BMP-2 treatment ("B") which is a positive control, the auraptene treatment ("Aur") increased the expression of both genes of ALP known as a marker of initial osteoblast differentiation and mouse osteocalcin known as a marker of later osteoblast differentiation compared with control ("-") (FIG. 5A, FIG. 5B).

Figure 5C:
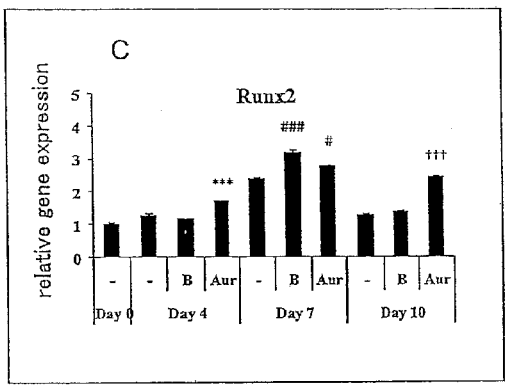
FIG. 5C is a figure showing the action of auraptene on the expression of an bone formation-related gene (Runx2). Explanation of the graph is the same as in FIG. 5A.
Figure 5D:
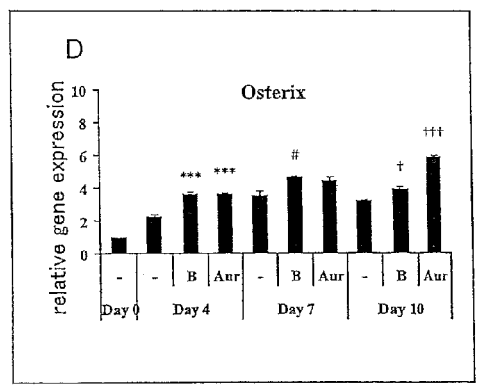
FIG. 5D is a figure showing the action of auraptene on the expression of an bone formation-related gene (osterix). Explanation of the graph is the same as in FIG. 5A.

(2) Expression of Transcription Factors Important for Osteoblast Differentiation From analyse using knockout mice and the like, Runx 2 and Osterix, both of which are transcription factors, are known to play an important role on osteoblast differentiation. As is the case with the BMP-2 treatment ("B") which is a positive control, the auraptene treatment ("Aur") increased the expression of both genes of Runx 2 and Osterix compared with control ("-") (FIG. 5C, FIG. 5D).

(3) Expression of BMP Genes

Figure 5E:
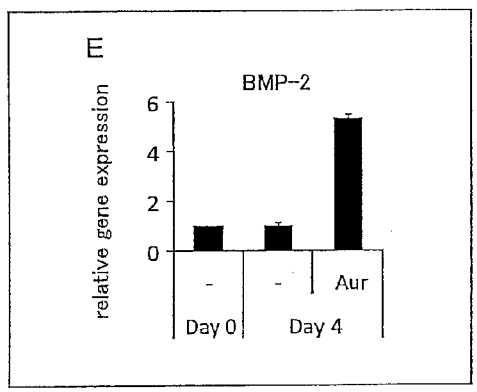
FIG. 5E is a figure showing the action of auraptene on an bone formation-related gene (the expression of BMP-2). Explanation of the graph is the same as in FIG. 5A.
Figure 5F:
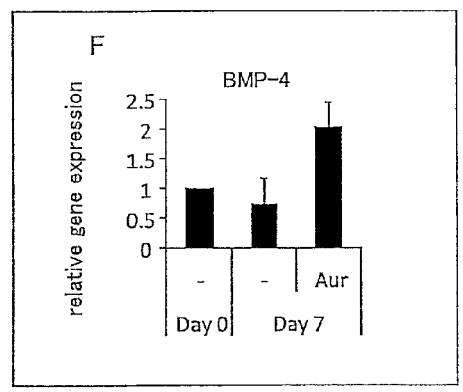
FIG. 5F is a figure showing the action of auraptene on the expression of an bone formation-related gene (BMP-4). Explanation of the graph is the same as in FIG. 5A.
Figure 6A:
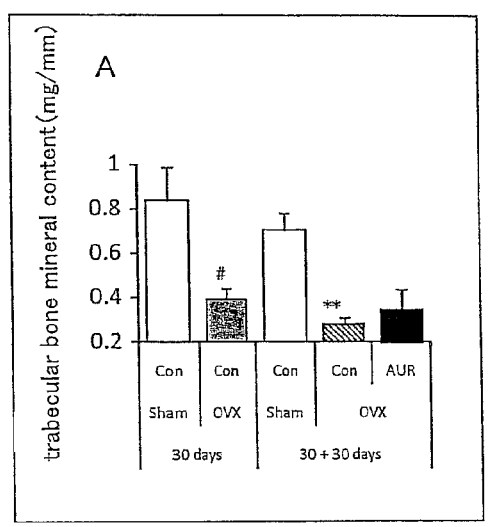
FIG. 6A is a figure showing the bone formation-promoting action (the effects on the trabecular bone mineral density) of auraptene in vivo. In each panel of FIGS. 6A to 6D, "Con" represents control, "AUR" represents auraptene administration, "Sham" represents sham operation, and "OVX" represents ovariectomy. Compared with "Sham" and "Con" after 30 days, # represents a significant difference of p<0.05 and ## represents a significant difference of p<0.005. Compared with "Sham" and "Con" after 30 days+30 days, * represents a significant difference of p<0.05 and ** represents a significant difference of p<0.005.
Figure 6B:
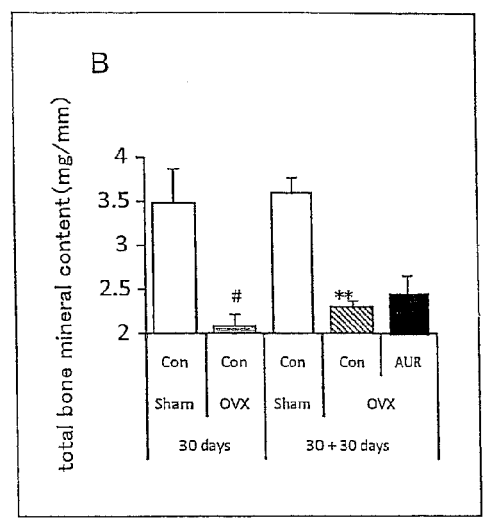
FIG. 6B is a figure showing the bone formation-promoting action (the effects on the total bone mineral density) of auraptene in vivo. Explanation of the graph is the same as in FIG. 6A.
Figure 6C:
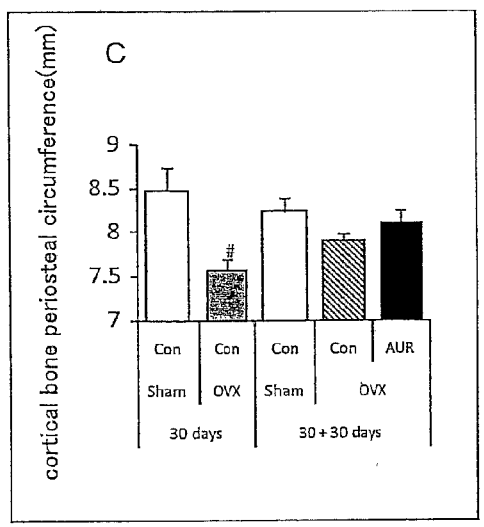
FIG. 6C is a figure showing the bone formation-promoting action (the effects on cortical bone periosteal circumference) of auraptene in vivo. Explanation of the graph is the same as in FIG. 6A.
Figure 6D:
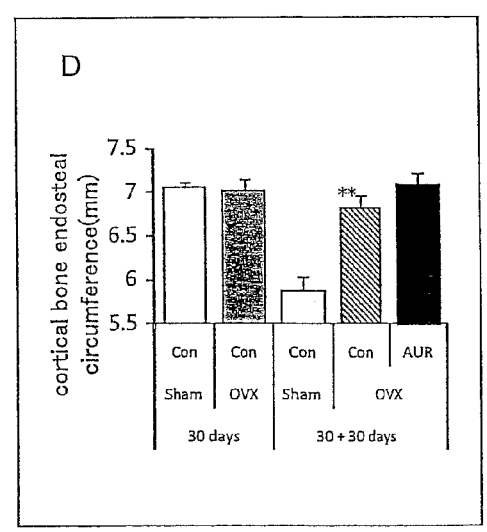
FIG. 6D is a figure showing the bone formation-promoting action (the effects on cortical bone endosteal circumference) of auraptene in vivo. Explanation of the graph is the same as in FIG. 6A.

BMPs are strong osteoblast differentiation promoting cytokines and it is reported that their expression is involved in osteoblast differentiation promoting effects of various compounds. The auraptene treatment increased the expression of both genes of BMP-2 and BMP-4 compared with control ("-") (FIG. 5E, FIG. 5F).

Based on the results mentioned above, it was demonstrated that auraptene increased the expression of ALP and Osteocalcin, which are characteristic to osteoblasts, at the gene level. In addition, auraptene increased the gene expression of Runx 2 and Osterix, which are important transcription factors for osteoblast differentiation. Further, auraptene increased the gene expression of BMP-2 and BMP-4, which are cytokines strongly promoting osteoblast differentiation. These results show that auraptene increases the expression of Runx 2 and Osterix through inducing the production of BMPs, thereby promoting osteoblast differentiation.

6. Bone Formation-Promoting Effect In Vivo

Postmenopausal osteoporosis model mice were prepared by ovariectomy and test compounds were administrated to the mice with decreased bone mass, to examine the effects on bone formation in vivo level.

Slc; ddY mice (4 week-old, female) were purchased from Chubu Kagaku Shizai Co., Ltd. After 2 days, ovariectomy ("OVX") or sham operation ("Sham") was performed under Nembutal anesthesia. After the mice were bred for 1 month in order to decrease bone mass due to the progression in bone resorption, a part of mice in each group (OVX: N=5, Sham: N=3) were killed to collect the femurs. The rest of mice in the ovariectomy ("OVX") group were divided into two groups: solvent administration group ("OVX-Con": N=6) and auraptene administration group (50 mg/kg/day, oral administration, "OVX-AUR": N=6) and bred for another month together with the sham operation group (Sham-Con: N=6). Thereafter, the mice were killed to collect the femurs.

The bone mineral content density and the like of the collected femurs were measured by means of pQCT (peripheral Quantitative Computed Tomography) using a bone density measuring apparatus (trade name "XCT Research SA+", manufactured by Stratec Medizintechnik GmbH).

The results are shown in FIG. 6A to FIG. 6D.

The trabecular bone mineral density (FIG. 6A) and the total bone mineral density (FIG. 6B) of the mice in the ovariectomy ("OVX") group after one-month breeding period ("30 days") were significantly decreased compared with those in the sham operation ("Sham") group. The trabecular bone mineral density (FIG. 6A) and the total bone mineral density (FIG. 6B) of the mice in the auraptene administration group ("OVX-AUR") after an additional one month of breeding ("30+30 days") tended to be high compared with those in the solvent administration group after ovariectomy ("OVX-Con").

The cortical bone periosteal circumference and cortical bone endosteal circumference are known as indices of bone formation and bone resorption, respectively. In the auraptene administration group ("OVX-AUR"), both of the cortical bone periosteal circumference (FIG. 6C) and the cortical bone endosteal circumference (FIG. 6D) tended to be long compared with the solvent administration group ("OVX-Con") ("30+30 days"). From these facts, it is considered that the auraptene administration increases both bone formation and bone resorption, which indicates that increases in the trabecular bone mineral density and the total bone mineral density due to the auraptene administration are caused not by bone resorption inhibition, but by bone formation-promoting effect. Therefore, it is considered that auraptene promotes osteoblast differentiation in vivo, thereby promoting bone formation.

7. Effect on Osteoclast Differentiation

In order to clarify the effect on bone resorption, the effect on differentiation of osteoclasts which are cells responsible for bone resorption was examined.

RAW264 cells (mouse monocyte/macrophage cell line, cell No. RCB0535) were purchased from RIKEN Cell Bank. The osteoclast differentiation-inducing factor (RANKL) was obtained from Wako Pure Chemical Industries, Ltd. Others used were the same as above.

RAW264 cells were suspended in α-MEM and plated in a 96-well microplate at a concentration of $3×10^3$ cells/well. The compounds of the present invention at each concentration and the osteoclast differentiation-inducing factor (RANKL) were added at 50 ng/ml and the cells were cultured for 3 days in an incubator at 37° C. and 5% $CO_2$. After incubation, the cells were fixed with a 10% formalin solution and refixed with 100% ethanol.

After the dishes were dried, as an index of differentiation, the activity of tartrate-resistant acid phosphatase (TRAP), a marker enzyme of osteoclasts, was measured by the following method.

For measurement of the TRAP activity, a buffer containing 10 mM tartrate and 50 mM citrate of pH 4.6, with 3.7 mM p-nitrophenylphosphate as a substrate, was used. The buffer was dispensed in each well of the 96-well microplate (100 μl/well) and allowed to react at 37° C. for 30 minutes. Thereafter, 100 μl of 0.1 N sodium hydroxide was added to terminate the reaction, followed by measurement of the absorbance at 405 nm with a plate reader. Each absorbance was determined to be the TRAP activity, and the value calculated by taking control as 100 was shown.

In addition, after similarly cultured, the cells were counted by a conventional method using a MTT reagent, and the value calculated by taking the control as 100 was shown.

Figures 1, 7:
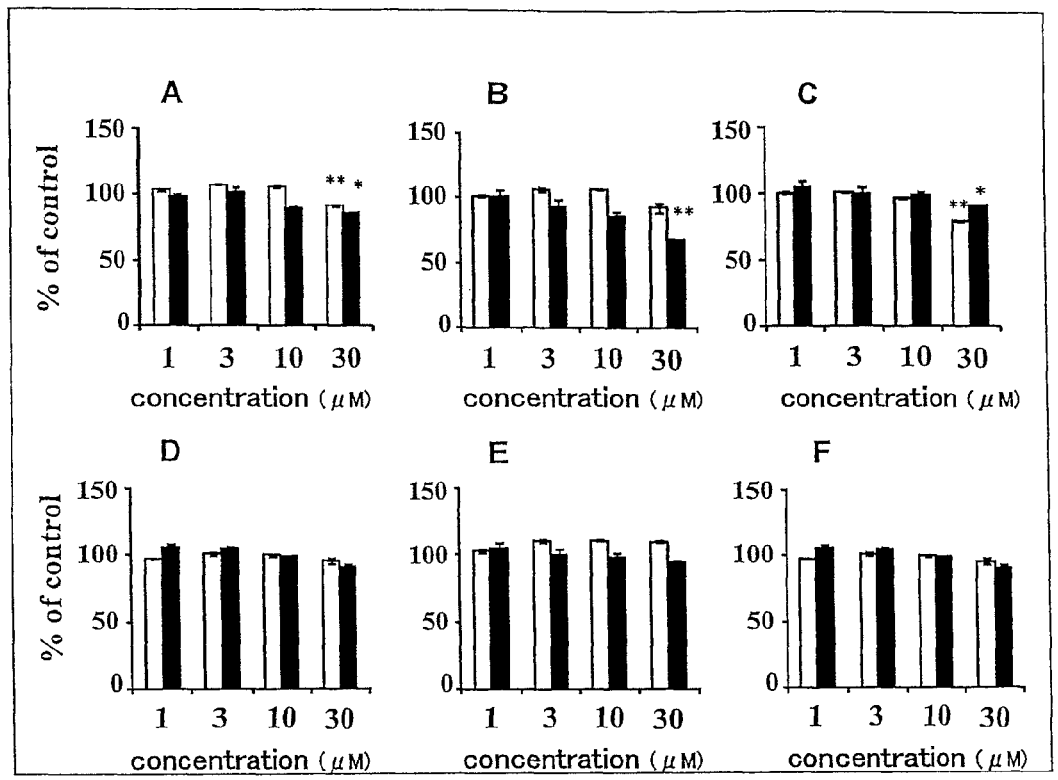
Figures 2, 7:
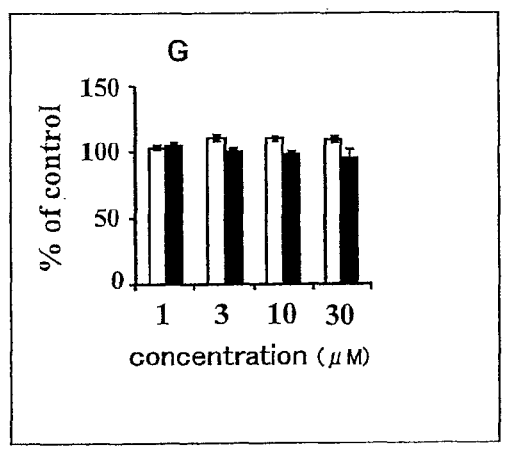

The results are shown in FIG. 7-1 and FIG. 7-2. Auraptene, as well as all coumarin compounds tested, did not show a significant influence on the cell number. In addition, any action specific to the TRAP activity as an index of osteoclast differentiation was not observed. These results indicate that auraptene and coumarin analogues thereof do not affect osteoclast differentiation, demonstrating that auraptene and coumarin analogues thereof do not exert an effect on bone resorption. Consequently, it is supported by these results too, that the effects in animal models do not result from bone resorption inhibition, but from bone formation-promotion.

This application is based on Japanese Patent Application No. 2010-046999 filed on Mar. 3, 2011, and the entire disclosure and claims of Japanese Patent Application No. 2010-046999 are included in this specification.

The invention claimed is:

1. A method for promoting osteoblast differentiation comprising administering to a subject in need thereof a pharmaceutical composition comprising a compound represented by the following formula 2:

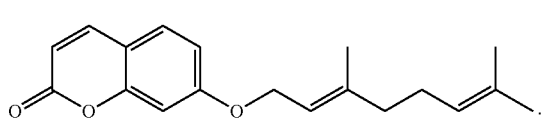

Formula 2

2. A method for promoting osteoblast differentiation comprising administering to a subject in need thereof a pharmaceutical composition comprising a compound represented by any of the following formulae 3 to 9:

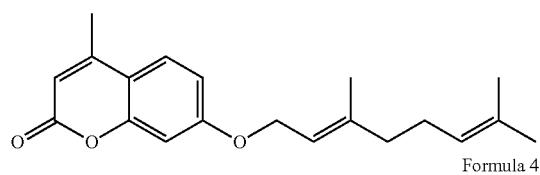

Formula 3

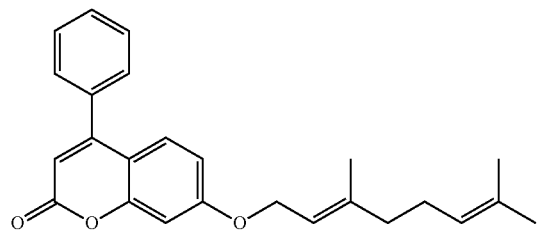

Formula 4

Formula 5
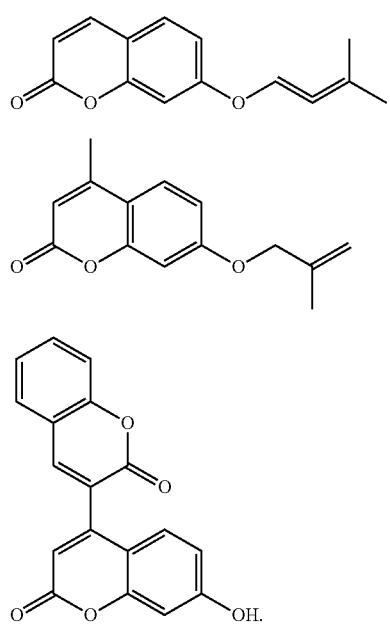
Formula 6
Formula 9
3. The method for promoting osteoblast differentiation according to claim 2, wherein the compound represented by the following formulae 3, 5, 6, or 9:
Formula 3
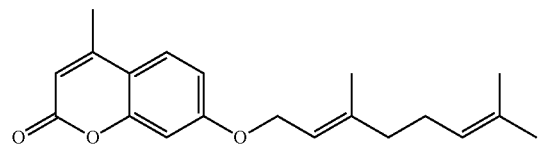
Formula 5
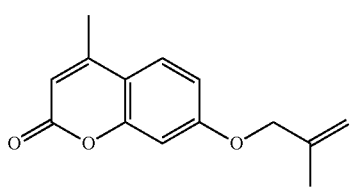
Formula 6
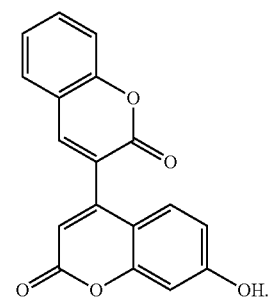
Formula 9
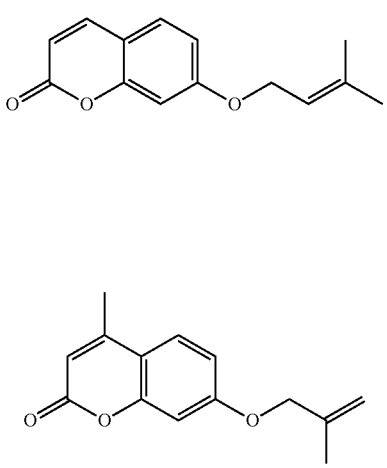
* * * * *

UNITED STATES PATENT AND TRADEMARK OFFICE
CERTIFICATE OF CORRECTION

PATENT NO. : 8,729,279 B2  Page 1 of 2
APPLICATION NO. : 13/581975
DATED : May 20, 2014
INVENTOR(S) : Je-Tae Woo et al.

It is certified that error appears in the above-identified patent and that said Letters Patent is hereby corrected as shown below:

In the Claims:

In Column 21, claim number 2, line number 1, replace

Formula 5

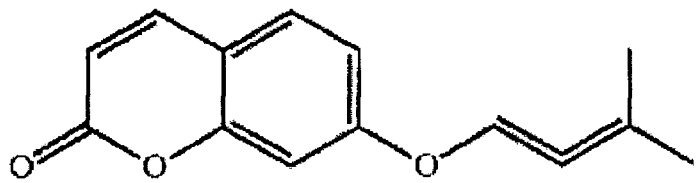

with

Formula 5

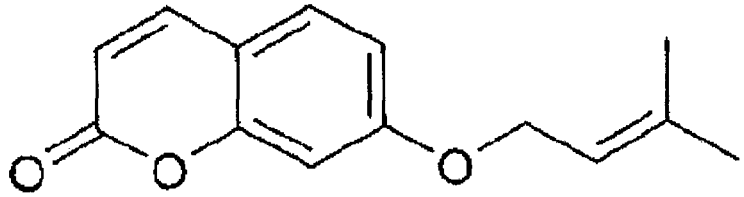

In Column 22, claim number 3, line number 20, insert

--Formula 7

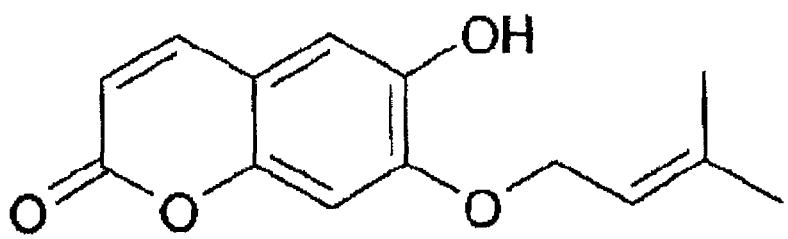

Signed and Sealed this
Twenty-first Day of October, 2014

Michelle K. Lee
*Deputy Director of the United States Patent and Trademark Office*

CERTIFICATE OF CORRECTION (continued)
U.S. Pat. No. 8,729,279 B2

Formula 8

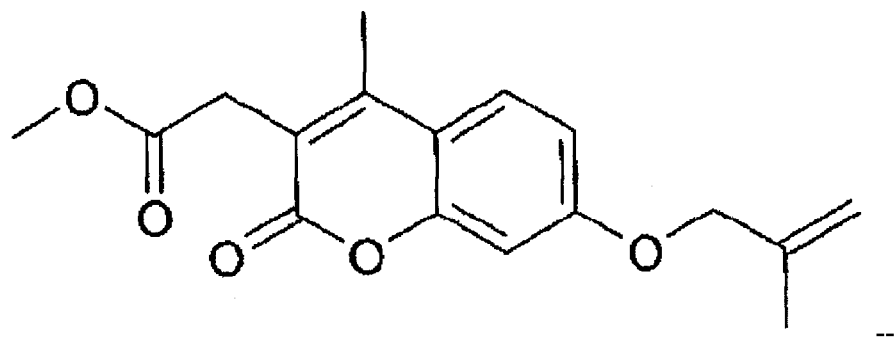

after

--Formula 6

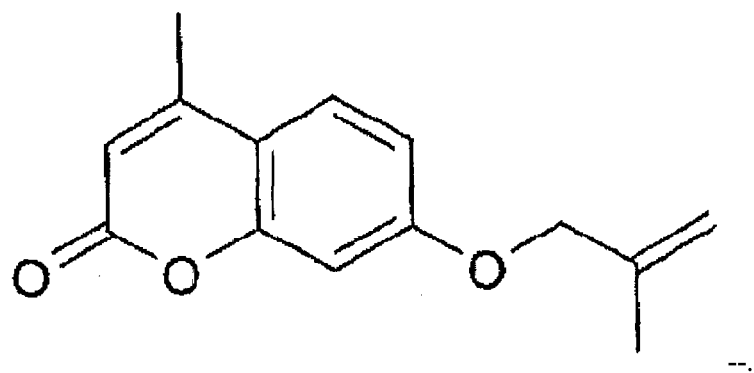

--.